(12) United States Patent
Freundlich et al.

(10) Patent No.: US 6,178,220 B1
(45) Date of Patent: Jan. 23, 2001

(54) CT SYSTEMS WITH OBLIQUE IMAGE PLANES

(75) Inventors: David Freundlich, Haifa; Alex Zaslavsky, Nesher; David Ruimi, Natanya, all of (IL)

(73) Assignee: Marconi Medical Systems Israel Ltd., Haifa (IL)

(*) Notice: Under 35 U.S.C. 154(b), the term of this patent shall be extended for 0 days.

(21) Appl. No.: 09/319,062

(22) PCT Filed: Jan. 29, 1997

(86) PCT No.: PCT/IL97/00038

§ 371 Date: Oct. 18, 1999

§ 102(e) Date: Oct. 18, 1999

(87) PCT Pub. No.: WO98/24063

PCT Pub. Date: Jun. 4, 1998

(30) Foreign Application Priority Data

Nov. 28, 1996 (IL) .................................................. 119714

(51) Int. Cl.⁷ ...................................................... A61B 6/03
(52) U.S. Cl. .................................. 378/4; 378/15; 378/17; 378/94
(58) Field of Search ........................... 378/4, 15, 17, 378/20, 901; 382/131

(56) References Cited

U.S. PATENT DOCUMENTS

| 4,495,645 | 1/1985 | Ohhashi | 382/131 |
| 4,674,046 | 6/1987 | Ozeki et al. | 382/131 |
| 5,431,161 | 7/1995 | Ryals | 600/425 |
| 5,524,130 | 6/1996 | Ohhashi | 378/15 |
| 5,633,951 * | 5/1997 | Moshfegi . | |

FOREIGN PATENT DOCUMENTS

| 0 504 855 | 9/1992 | (EP) . |
| 0 383 232 | 10/1996 | (EP) . |
| 0 464 645 | 5/1997 | (EP) . |
| WO 94/20922 | 9/1994 | (WO) . |

OTHER PUBLICATIONS

Elscint Ltd.; "Elscint Report"; vol. 8, No. 2; pp. 4–5; Jun. 1996.

* cited by examiner

*Primary Examiner*—David V. Bruce
(74) *Attorney, Agent, or Firm*—Fenster & Company Patent Attorneys, Ltd.

(57) ABSTRACT

A method for reconstructing one or more non-axial image slices in a CT scanner, comprising: acquiring X-ray attenuation data over an axial range; and processing the attenuation data to determine CT values at a plurality of points along one or more surface corresponding respectively to each one or more non-axial image slices, wherein processing the attenuation data comprises back-projecting the data directly to the plurality of points along each of the one or more surfaces.

29 Claims, 4 Drawing Sheets

CT SYSTEMS WITH OBLIQUE IMAGE PLANES

RELATED APPLICATION

The present application is a U.S. national stage application of PCT application PCT/IL97/00038, filed Jan. 29, 1997.

FIELD OF THE INVENTION

The present invention relates generally to computerized tomographic (CT) imaging, and specifically to methods of reconstructing CT images along oblique image planes.

BACKGROUND OF THE INVENTION

CT scanners known in the art typically produce a plurality of parallel, planar image slices. The slice planes are generally defined by the plane of revolution of an X-ray tube, which is mounted on an annular gantry, so as to revolve about a subject being imaged. The subject lies on a bed, which is translated through the gantry along a scan axis. An array of X-ray detectors on the opposite side of the subject from the X-ray tube receives radiation transmitted through the subject. Each of the detectors generates signals proportional to the attenuated X-ray flux incident thereon. These signals are pre-processed to produce attenuation data, which are filtered and back-projected to determine CT values, representing image data, at a plurality of points in each of the plurality of planar image slices. These slices, which are located at a corresponding plurality of mutually-spaced axial positions, are taken together to provide a three-dimensional image of all or a part of the subject's body.

Usually the scan axis is approximately parallel to the long axis of the subject's body and perpendicular to the plane of revolution of the tube, so that the image slices represent a series of axial cross-sections through the body. Such slices are known as "axial slices." Axial slices commonly have a relatively high image resolution, for example 1 mm or less, within the plane of each slice, but a poorer resolution in the axial dimension, for example about 5 mm. This axial resolution is known as the slice "thickness." Typically the spacing between one axial slice and the next is set to be approximately equal to the slice thickness.

In some cases, however, a physician examining the subject wishes to observe oblique. rather than axial, image slices, intersecting the body along planes that are angled with respect to the body's long axis. Several methods are known in the art for enabling such oblique slices to be viewed.

In some CT scanners, oblique image slice data are captured by angling the bed relative to the plane of revolution of the tube, by swiveling the bed and/or by tilting the tube's plane of revolution. The mechanisms required to implement and control the tilt and swivel capabilities, however, add substantially to the cost of the CT scanner. Furthermore, mechanical and other practical considerations limit the tilt and swivel angles to no more than about 30°, so that more oblique image slices, such as sagittal or coronal slices through the subject's body, cannot be directly produced.

Alternatively, an oblique image slice may be reconstructed by interpolation of the CT values in the original axial image slices. Such interpolative methods are well known in the art. as described, for example, in U.S. Pat. No. 4,674,046, to Ozeki et al., which is incorporated herein by reference. To view an oblique image slice according to this method, a user of a CT system, such as a physician, must generally operate the system first to acquire and display a full series of axial images, covering all or at least a substantial portion of the subject's body. Only afterwards may the user input to the system the position and orientation of the desired oblique slice.

Each oblique slice to be reconstructed in this manner intersects a number of the axial slices. For each of a plurality of points in the oblique slice, an interpolated CT value is found by taking a weighted sum of the CT values at a group of neighboring points in one or more of the original axial image slices. When using this method, typically only the CT values are stored in computer memory, while the attenuation data that were used to derive the CT values are deleted in order to conserve memory space.

Derivation of oblique slices by interpolation of axial images has several serious drawbacks. Interpolation of the CT values inevitably leads to a loss of resolution in the oblique image slice, since the axial resolution of the data is low. The interpolated oblique image slices generally appear to have poorer image quality, particularly higher noise level, and may exhibit artifacts, such as stair-step effects. Furthermore, the interpolation operation is computation-intensive and, consequently, time-consuming, and requires a very large computer memory.

SUMMARY OF THE INVENTION

It is an object of the present-invention to provide methods for reconstructing oblique CT image slices rapidly and with improved image quality.

It is another object of the present invention to provide methods for reconstructing oblique CT image slices at substantially any desired slice angle, without the necessity of introducing swivel or tilt into the CT system.

In one aspect of the present invention, CT images are directly reconstructed along sagittal and coronal planes, for example, along sagittal and coronal cuts through the spinal cord.

In another aspect of the present invention, CT images are reconstructed along non-planar cuts through the body of a subject, for example, along cuts that follow anatomical features, such as the spinal cord or major blood vessels.

In yet another aspect of the present invention, the thickness of each image slice, i.e., the resolution of the slice in a direction perpendicular to the slice plane, is set to substantially any desired value, within geometrical limits of the CT scanner used to acquire the attenuation data.

In still another aspect of the present invention, multiple oblique slices are reconstructed having differing slice thickness, for example, to provide a CT image of the head of a subject including multiple slices of varying resolution from a single scan.

It is yet a further object of some aspects of the present invention to provide methods for reconstruction of oblique CT image slices directly from X-ray attenuation data, without first back-projecting the data to obtain CT values in full axial image slices, thus reducing the computing time needed and the consumption of film involved in obtaining desired oblique slice images.

Still another object of some aspects of the present invention is to allow a user of a CT system to specify one or more desired oblique image slices before scanning the body of a subject, whereupon acquisition and processing of X-ray attenuation data by the system are optimized to produce the oblique slice with suitable resolution while minimizing radiation dosage to the subject and scanning and computing time.

In one aspect of the present invention, the user may specify, a non-planar cut through the body, for example, a cut that follows the spinal cord.

In another aspect of the present invention, the user may specify a plurality of non-parallel oblique slices, for example, so as to image one or more disc spaces between the subject's vertebrae. One or several of the plurality of slices pass through or are adjacent to each of the one or more disc spaces. The slices are oriented so that the plane of each slice is substantially perpendicular to the axis of the subject's spine at the disc space where the slice is located.

It is an additional object of some aspects of the present invention to provide methods for reconstructing oblique slices directly from X-ray attenuation data acquired by a spiral-scan CT system.

In preferred embodiments of the present invention, a spiral-scan CT scanner comprises an X-ray tube, mounted to revolve on an annular gantry about a bed on which a subject lies. and a detector array. The bed is advanced through the gantry along a translation axis that is generally parallel to the long axis of the subject's body. The X-ray tube thus describes a (generally helical trajectory about the subject's body and irradiates the subject from multiple positions, or "views," along this trajectory. Preferably, the translation axis is substantially perpendicular to a plane of revolution of the X-ray tube, although it will be appreciated that the principles of the present invention may similarly be applied to CT systems in which the bed is angled relative to the plane of revolution, as are known in the art.

The detector array preferably comprises one or more parallel rows of X-ray detector elements, each row having a long axis disposed in a generally circumferential direction with respect to the long axis of the subject's body. The detector elements receive radiation that has passed through the subject's body at each of the views and generate signals responsive to attenuation of the X-rays. Preferably, the detector array is mounted on the gantry, opposite the X-ray tube, to revolve around the bed along with the tube as in "third-generation" CT scanners. Alternatively, the detector array comprises an annular ring of detector elements, which surrounds the subject and is held in a substantially stationary position while the tube revolves, as in "fourth-generation" scanners. The principles of the present invention, as described herein with reference to various preferred embodiments, will be understood to apply equally to third- and fourth-generation scanners as well as to other types of scanners known in the art.

In some preferred embodiments of the present invention, a user of the CT scanner, for example, a physician, selects a desired slice orientation, slice spacing and scan extent for a sequence of slices to be reconstructed. The slice orientation is defined by a slice axis passing through the body of the subject at any desired slice angle, wherein the slice angle is taken to be zero for axial slices, as described above. It will be understood that the slice angle is generally a three-dimensional spatial angle, which may be expressed, for example, in terms of angular azimuth, elevation and roll coordinates relative to the scan axis. The terms "slice orientations" and "slice angle" as used herein should be understood in this context.

Preferably, the slice spacing along the slice axis direction is set to be generally equal to or less than the slice thickness, defined as the resolution of the slice in the direction of the slice axis. The slice spacing may vary from one slice to another. The scan extent is defined by the distance along the scan axis between a leadings edge of the first slice and a trailing edge of the last slice in the sequence.

Alternatively, the user may choose to view only a single slice, with a desired orientation and thickness. The principles of the present invention, to be described below, are equally applicable to this case.

In some preferred embodiments of the present invention, the user selects one or more slices to be reconstructed by indicating a curved path within the body, preferably by viewing a preliminary image of the body acquired by the CT scanner. Methods of indicating the path and selecting the slices are described in the "Elscint Report," vol. 8, no. 2, published June, 1996, by Elscint Ltd., which is incorporated herein by reference. The user may select for reconstruction oblique slices that are generally perpendicular to the path. Additionally or alternatively, the user may select a non-planar cut that is defined by the curved path, preferably a curved surface within the body that includes the path, and a planar image may be reconstructed of this surface.

It will be understood that although preferred embodiments are described herein with reference to planar oblique slices, the principles of the present invention may be similarly applied to directly reconstruct planar images of such curved surfaces. In the context of the present patent application, the term "surface" will be taken to refer collectively to both planar, oblique image slices and non-planar image surfaces.

In preferred embodiments of the present invention, the non-transverse image surface or each of a sequence of such surfaces is divided into a plurality of parallel back-projection lines. Each such line is defined by the intersection of the plane of the surface with one of a plurality of axial planes through the body. The distance between the axial planes is chosen in accordance with the slice angle (i.e., the angle between the surface and the axial slices) and the desired resolution and image quality, but is preferably less than or equal to the axial slice desired resolution and image quality, but is preferably less than or equal to the axial slice thickness. Preferably, the same plurality of axial planes is used to define respective back projection lines in each of the sequence of slices.

For each view, as the X-ray tube advances along its helical path, each of the one or more rows of the detector array generates a corresponding line attenuation signal. These signals are preprocessed and, preferably, filtered, as is known in the art. The resultant line attenuation data are interpolated to generate an effective attenuation value for each of a plurality of rays within each axial plane associated with the back projection lines.

Preferably, the filtered line attenuation data are stored in the scanner's memory, for example, on disk, as the filtered data generally occupies substantially less memory volume than would the "raw" or preprocessed signals. The stored, filtered data may then be interpolated to generate effective attenuation values for the desired axial planes within an axial range covered by the helical scan path. In this manner, the principles of the present invention may be applied to reconstruct images of non-transverse surfaces that are designated both before and after the X-ray attenuation data are acquired.

In preferred embodiments of the present invention, for each of a plurality of points along each of the back-projection lines in each of the oblique slices, the effective attenuation values for the rays passing through the point are back-projected to determine a CT value at the point. This back-projection is performed using algorithms similar to those known in the art, except that the CT values are determined substantially only along the back-projection lines and not in the remainder of the axial planes. For each oblique slice, the CT values for the corresponding plurality of back-projection lines are used to directly reconstruct and display a corresponding oblique slice image.

Back-projecting to determine the CT values only along the back-projection lines, rather than in the entire axial plane, saves considerable computation time. Preferably, the back-projection operation is performed using a coordinate system in the axial planes that is rotated so that one of the coordinate axes is parallel to the back-projection lines, so as to further simplify the calculation. Further preferably, the axes of the coordinate system are shifted for computing each of the back-projection lines, so that one of the axes coincides with the back-projection line.

Preferably, after the oblique slice image has been reconstructed, as described above, the image is further post-processed to enhance the visibility of image details and remove artifacts. Most methods of CT image post-processing known in the art may be used for this purpose, although some methods must be modified to account for the oblique slice angle from the scan axis. For example, ring artifacts, which commonly appear in axial CT images and are recognized and removed from the images during post-processing, will appear in the oblique slice images as ellipses or as portions of ellipses. These ellipse artifacts will be centered at a point in the image corresponding to the center of revolution of the X-ray tube and will have a known ratio of major to minor axes and a known angular orientation of these axes within the oblique slice, dependent only on the slice angle. Preferably, an image processing computer associated with the CT scanner is programmed to recognize and remove from oblique slice images ellipses centered at the center of revolution and having the known major-to-minor-axis ratio.

In some preferred embodiments of the present invention, the plurality of axial planes are mutually spaced by a distance that is generally equal to or less than half the axial slice thickness. The slice thickness is generally dependent, inter alia, on the pitch of the spiral path described by the X-ray tube and may thus be controlled by varying the pitch. Additionally or alternatively, other factors that influence the slice thickness, for example, collimation of the X-rays emitted by the X-ray tube, may be varied to control the slice thickness. The axial plane spacing may be set, in a spiral-scan CT system, to substantially any suitable value.

In some preferred embodiments of the present invention, multiple parallel, mutually-adjacent oblique slices are reconstructed, wherein the slices are spaced by a distance substantially less than the axial slice thickness. These slices are "fused," i.e., their CT values are added together and/or averaged, to produce a sum slice of improved image quality. Preferably, the multiple oblique slices are chosen and fused in such a manner that the sum slice has isotropic resolution, substantially independent of the angle along which the resolution is measured.

Additionally or alternatively, preprocessed or prepro-cessed and filtered attenuation data corresponding to multiple, closely-spaced axial planes may similarly be fused by adding them together and/or averaging them, preferably by taking a weighted average. The fused data are back-projected to produce one or more oblique image slices, as described above.

It will be understood that the principles of the present invention may be generally applied to any type of spiral-scan CT system known in the art. including both third- and fourth-generation type scanners, systems using either 180° or 360° image reconstruction, and scanners for industrial, as well as various medical, uses.

Furthermore, although preferred embodiments are described herein with reference to spiral-scan CT systems, it will be appreciated that the principles of the present invention may also be applied to axial-scan CT systems, which are well known in the art, In such systems, the bed is advanced in alternation with the revolution of the X-ray tube, so that attenuation data are acquired for multiple views in each of a plurality of distinct axial planes. These attenuation data may be back-projected in accordance with the present invention, to reconstruct the oblique image slices.

There is therefore provided, in accordance with a preferred embodiment of the present invention, a method for reconstructing one or more non-axial image slices in a CT scanner, including:

acquiring X-ray attenuation data over an axial range; and processing the attenuation data to determine CT values at a plurality of points along one or more surfaces corresponding respectively to each of one or more non-axial image slices, wherein processing the attenuation data comprises back-projecting the data directly to the plurality of points along each of the one or more surfaces.

Preferably, acquiring the data over the axial range includes acquiring data over a range defined by an axial extent of the one or more non-axial image slices, and back-projecting the data includes back-projecting the data to determine CT values substantially only at the plurality of points in each of the one or more non-axial planes.

Preferably, acquiring the X-ray attenuation data over the axial range includes acquiring X-ray attenuation data along a spiral scan path traversing the range.

Preferably, reconstructing the one or more non-axial image slices includes reconstructing images of one or more curved surfaces, and processing the attenuation data to determine CT values along the one or more surfaces includes processing the data to determine CT values at points along the curved surfaces.

Alternatively or additionally, reconstructing the one or more non-axial image slices includes reconstructing planar, oblique image slices, oriented obliquely relative to an axis of the scanner, and processing the attenuation data to determine CT values along the one or more surfaces includes processing the data to determine CT values at points in one or more oblique planes defined by the image slices.

Preferably, the method described a boy-e-further includes selecting a plurality of axial planes, which define a plurality of lines at the respective intersections of the axial planes with the one or more non-axial slices, along which lines the CT values are determined.

There is further provided, in accordance with a preferred embodiment of the present invention, a method for reconstructing one or more non-axial image slices in a CT scanner. including:

selecting a plurality of axial planes, having a predetermined axial spacing therebetween, thereby defining a plurality of lines at the intersections of the planes with the one or more non-axial image slices;

acquiring X-ray attenuation data along a spiral scan path having a known pitch traversing an axial range defined by the plurality of axial planes; and processing the X-ray attenuation data to determine CT values directly at a plurality of points along the plurality of lines.

Preferably, processing the X-ray attenuation data includes back-projecting the attenuation data to determine CT values substantially only at the plurality of points along the plurality of lines.

Further preferably, processing the X-ray attenuation data includes fusing attenuation data from multiple, mutually-adjacent planes among the plurality of axial planes to produce sum data, and back-projecting the attenuation data includes back-projecting the sum data.

Preferably processing the attenuation data includes filtering the attenuation data before back-projecting the data, and data that are not used to determine the CT values along the plurality of lines are eliminated from the filtering operation.

Preferably, processing the attenuation data includes interpolating the attenuation data to find effective attenuation values in the plurality of axial planes.

Preferably, selecting the plurality of axial planes includes selecting axial planes mutually spaced by a distance substantially less than the thickness of an axial image slice corresponding to one of the axial planes, more preferably by a distance less than or equal to half the thickness of the axial image slice, and most preferably by a distance less than or equal to one third the thickness of the axial image slice.

Preferably, the method described above further includes processing the X-ray attenuation data to determine CT values at additional points in a vicinity of one or more of the lines in at least one of the axial planes, and detecting artifacts, preferably ring artifacts, in the at least one of the axial planes using the CT values at the additional points. Further preferably, the artifacts are removed from at least one of the non-axial image slices.

Preferably, reconstructing the one or more non-axial image slices includes reconstructing images of one or more curved surfaces, and processing the attenuation data to determine CT values along the one or more surfaces includes processing the data to determine CT values at points along the curved surfaces.

Alternatively or additionally, reconstructing the one or more non-axial image slices includes reconstructing planar, oblique image slices, oriented obliquely relative to an axis of the scanner, and processing the attenuation data to determine CT values along the one or more surfaces includes processing the data to determine CT values at points in one or more oblique planes defined by the image slices.

Preferably, artifacts are detected in the one or more oblique image slices by identifying an ellipse in at least one of the oblique image slices, preferably ba finding an ellipse having a known ratio of major to minor axes, and/or finding an ellipse having a known angular orientation of its axes in the plane of one of the one or more oblique image slices.

There is additionally provided, in accordance with a preferred embodiment of the present invention, a method for reconstructing a plurality of non-axial image slices in a CT scanner, including:

selecting a position and an orientation for each of the plurality of non-axial slices; and reconstructing each of the slices as described above, wherein selecting the plurality of axial planes includes selecting at least one common axial plane for reconstructing at least a portion of each of two of the plurality of non-axial slices.

Preferably, reconstructing the plurality of non-axial image slices includes reconstructing a plurality of planar, oblique slices, and selecting the position and the orientation for each of the plurality of non-axial slices includes selecting a common orientation for at least two of the oblique slices.

Further preferably, selecting the position and orientation for each of the plurality of oblique slices includes selecting a common orientation for a group of at least three of the oblique slices and selecting the positions of the slices so that the slices in the group are evenly spaced.

Additionally or alternatively, at least two of the commonly-oriented oblique slices are fused to produce an oblique sum slice, which preferably has angle-independent resolution.

Further alternatively, selecting the position and orientation for each of the plurality of oblique slices includes selecting a common orientation for a group of at least three of the oblique slices and selecting the positions of the slices so that the slices in the group are unequally spaced.

Attentively or additionally, selecting the position and orientation for each of the plurality of oblique slices includes selecting different orientations for at least two of the slices.

Preferably, processing the attenuation data to determine CT values includes pre-processing the attenuation data during a CT scan, storing the pre-processed data, and processing the stored data to determine the CT values, wherein pre-processing the data preferably includes filtering the data.

The present invention will be more fully understood from the following detailed discription of the preferred embodiments thereof, taken together with the drawings in which:

DETAILED DESCRIPTION OF PREFERRED EMBODIMENTS

Figure 1:
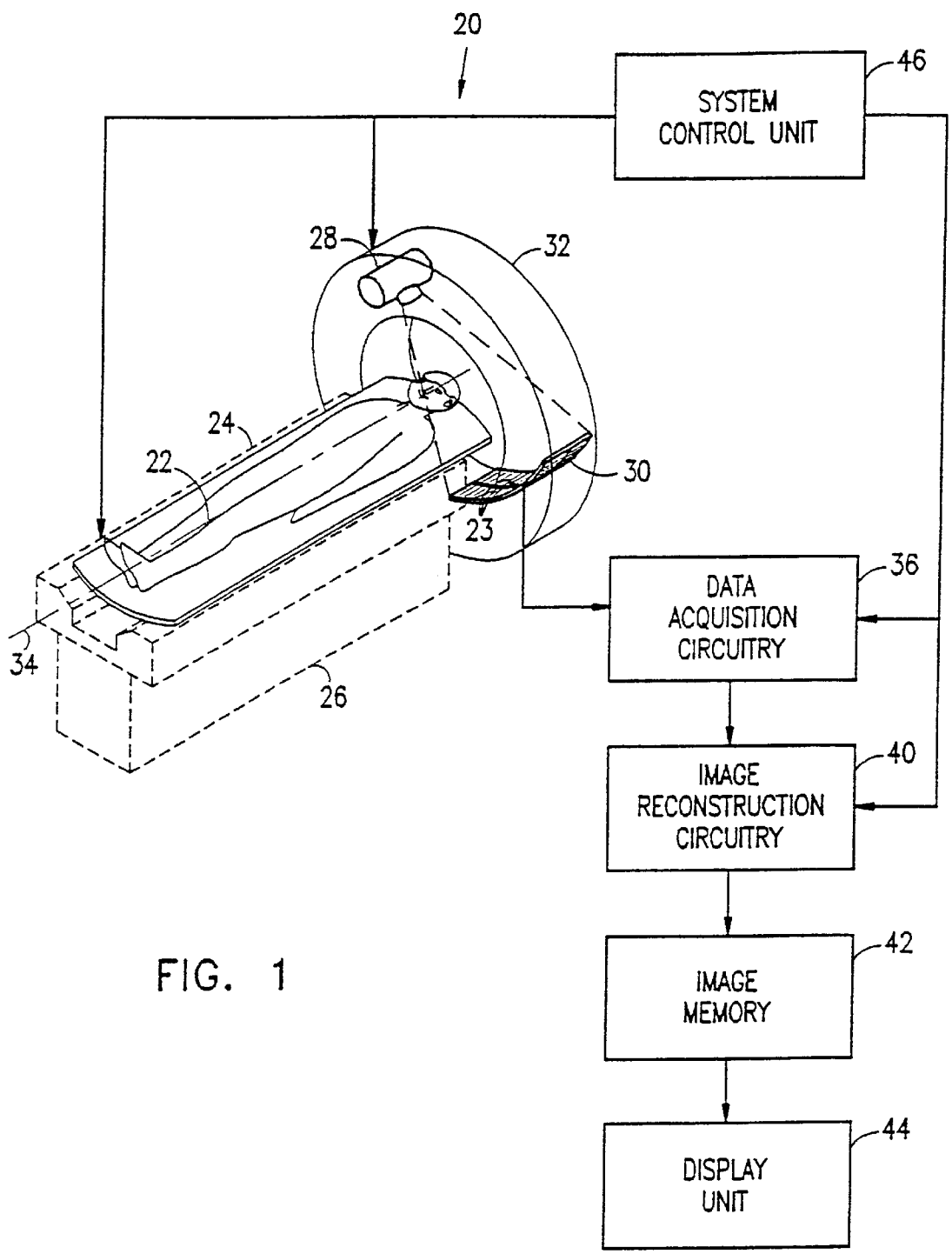
FIG. 1 is a schematic illustration of a helical-scan CT scanner, operative in accordance with a preferred embodiment of the present invention.

Reference is now made to FIG. 1, which shows a CT scanner 20, operative in accordance with a preferred embodiment of the present invention. Scanner 20 comprises a bed 24, supported by a base 26, on which bed a subject 22 lies while his body is being imaged by the scanner. Scanner 20 further comprises an X-ray tube 28, which irradiates subject 22, and a detector array 30, which receives X-rays from tube 28 and generates signals responsive to the attenuation of the X-rays in passing through the subject's body. Preferably, array 30 comprises one or more parallel rows of X-ray detector elements 23. Tube 28 and array 30 are mounted on an annular gantry 32, so as to revolve about subject 22. Simultaneously, bed 24 is advanced through gantry 32 along an axis 34. Axis 34 is generally parallel to the long axis of the subject's body and is preferably parallel to the axis of revolution of tube 28, although axis 34 may alternatively be angled relative to the axis of revolution.

Scanner 20 as pictured in FIG. 1 is of a type known in the art as a third-generation CT-scanner, characterized in that both tube 28 and detector array 30 revolve about subject 22. It will be appreciated, however, that the principles of the present invention and the methods of image reconstruction to be described below are equally applicable to other types of CT scanners, for example, fourth-generation CT scanners, in which the detector array forms a stationary ring, and only the X-ray tube revolves.

As tube 28 revolves and bed 24 advances, the tube describes a generally spiral path around axis 34. Preferably, bed 24 moves with substantially constant velocity, so that the spiral path has a constant pitch. At each of a plurality of selected locations of tube 28 along this path, data acquisition circuitry 36 acquires a "view," i.e., the circuitry receives signals from each element 23 of array 30 responsive to X-ray attenuation along a ray from tube 28 to the element.

Although CT scanner 20 is described here as operating in a spiral-scan mode, it will be appreciated that the scanner can also be made to operate in an axial-scan mode, in which bed 24 is advanced in alternation with the revolution of tube 28, as is known in the art. The principles of the present invention described below are generally also applicable to the axial scan mode of CT scanning.

For each view, data acquisition circuitry 36 preprocesses the signals, generally performing signal normalization and logarithm operations, as are known in the art, to derive an X-ray attenuation value corresponding to each of elements 23. Image reconstruction circuitry 40 receives these values and performs interpolation, filtering and back-projection operations, as will be described in greater detail below, to reconstruct planar images of surfaces within the body of subject 22. Alternatively, the circuitry 40 may first filter the preprocessed attenuation values, before interpolation. The filtered values may then be interpolated and back-projected immediately and/or stored in memory for later interpolation and back-projection.

As will be described below, the surfaces within the body of subject 22 may correspond to planar slices or to non-planar, curved cuts through the body. A plurality of these planar images may be produced, so as to produce three-dimensional CT images of the body. Preferably, these image slices are stored in image memory 42 and displayed by display unit 44, and they may be otherwise printed and/or processed as is known in the art.

A system control unit 46 controls the functioning of the various other elements of scanner 20, as well as receiving and implementing input commands from a user of the scanner, as will be described below.

Figure 2:
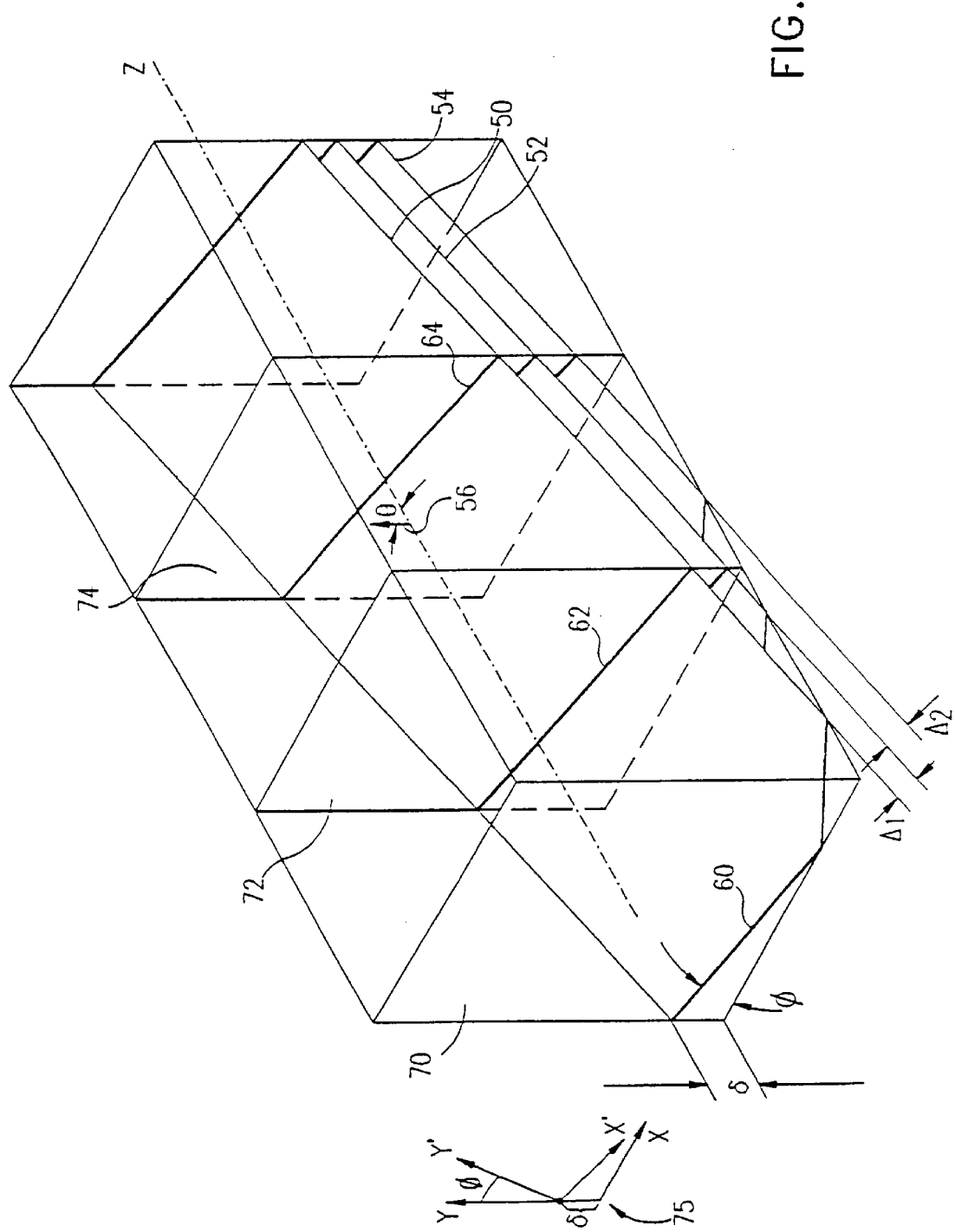
FIG. 2 is a schematic, isometric illustration of oblique image slices and axial planes in the scanner of FIG. 1, exemplifying aspects of a method for CT image reconstruction in accordance with a preferred embodiment of the present invention.

As illustrated schematically in FIG. 2, in preferred embodiments of the present invention, planar images produced by CT scanner 20, may correspond to oblique planar slices, for example, oblique slices 50, 52 and 54. Such oblique slices are taken along arbitrary planes, generally not perpendicular to axis 34. Slices 50, 52 and 54 are preferably mutually parallel and spaced by a distance $\Delta_1$ between slices 50 and 52, and a distance $\Delta_2$, between slices 52 and 54. The orientation of the planes of slices 50, 52 and 54 is defined by a slice axis 56, perpendicular to the planes of the slices, which deviates by an orientation angle θ from the Z-axis, which is defined by the axis of revolution of tube 28, as described above. It will be understood that θ represents a three-dimensional spatial angle, which may generally include angular elevation, azimuth and roll coordinates.

Preferably, although not necessarily, distances $\Delta_1$ and $\Delta_2$ are substantially equal and are also generally equal to the slice thicknesses, i.e., the resolutions of slices 50, 52 and 54 in the direction of axis 56. The orientation angle and the slice thicknesses can be set to any desired values, although the slice thickness is practically limited by the minimum image resolution of scanner 20, which depends on the size and spacing (including the circumferential width and the axial length) of detector elements 23 in array 30 and on the pitch of the spiral path described by tube 28. Furthermore, the minimum image resolution of the scanner is not generally isotropic, but is finer in the radial directions, within the plane of an axial slice, than in the axial direction. Therefore, the lower limit of the resolution of slices 50, 52 and 54 is also dependent on their orientation angle θ.

Preferably, a user of CT scanner 20, for example, a physician, selects a sequence of slices to be reconstructed, such as slices 50, 52, 54 and additional slices parallel to these slices, by setting the desired slice orientation angle θ, the slice thickness, and a desired scan extent, defined by the respective locations of the first and last slices in the sequence. Although the slices are preferably mutually parallel and of equal thickness, non-parallel slices and/or slices of varying thickness may also be produced from a single scan of scanner 20, in accordance with other preferred embodiments of the present invention. Such non-parallel slices may be arrayed along an arbitrarily-chosen curved path within the body, as described below. Methods for reconstructing non-parallel slices, slices of varying thickness, and images of non-planar surfaces are substantially the same as the methods described herein for reconstructing parallel oblique slices.

Figure 3:
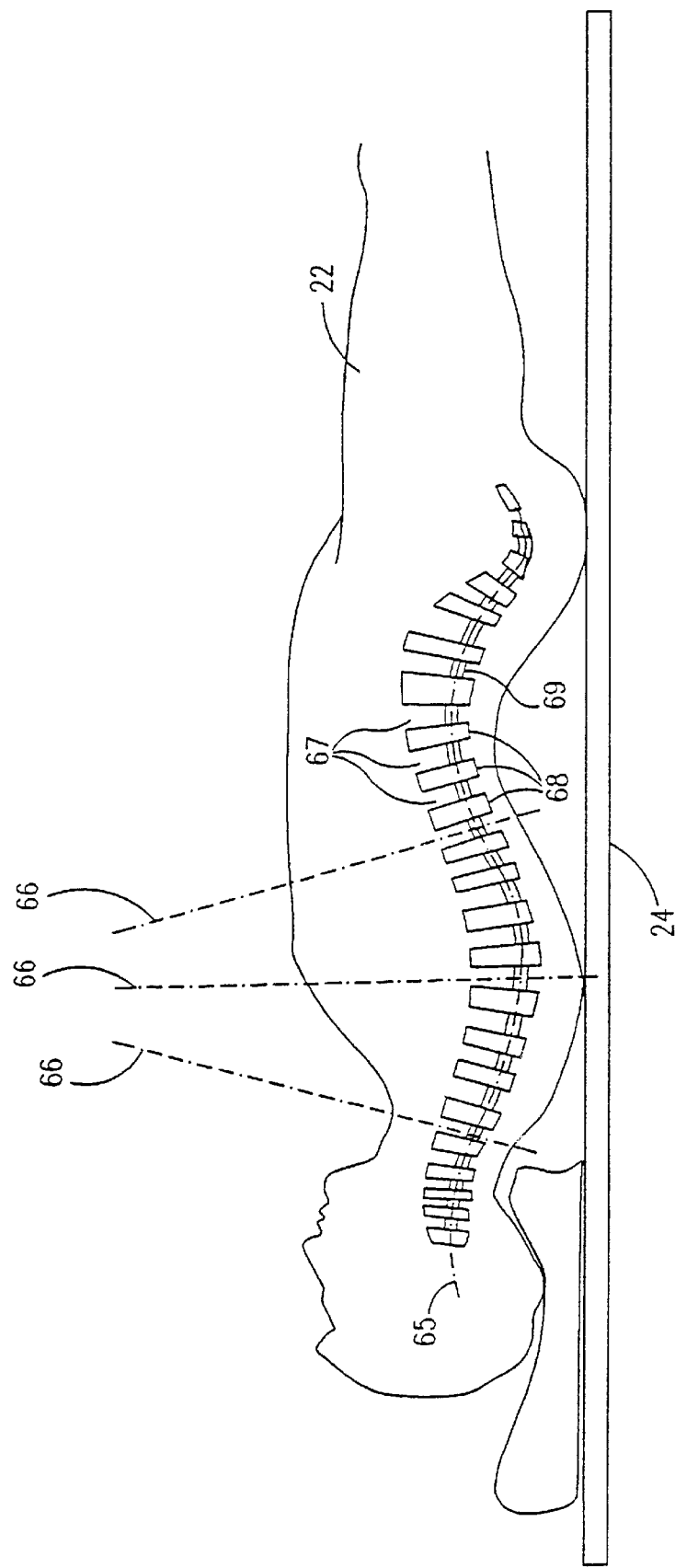
FIG. 3 is a schematic, sectional side view of a subject in the scanner of FIG. 1, illustrating positions and orientations of oblique and non-planar image surfaces, in accordance with a preferred embodiment of the present invention.

FIG. 3, for example, schematically illustrates the selection of multiple non-parallel oblique slices 66 for reconstruction, in accordance with one such preferred embodiment of the present invention; In this case, slices 66 are arrayed along a curved path 65, following the direction of spinal cord 69. Slices 66 are chosen so as to provide images of disc spaces 67, each intermediate a pair of vertebrae 68. For the best diagnostic view of disc spaces 67, each of slices 66 is preferably perpendicular to an axis defined by path 65 at the point of intersection of the slice therewith. Although the figure shows only a single slice 66 in each disc space 67, several parallel slices in each disc space could also be selected and reconstructed. The user's selection of path 65 and slices 66 may be entered graphically, for example, on a planar preliminary X-ray image of subject 22 produced by CT scanner 20.

Alternatively, the user may select a non-planar slice or surface within body 22 to be imaged, particularly a slice or surface following an anatomical feature, such as spinal cord 69. In this case, for example, an image may be produced by scanner 20 showing a curved surface that follows and includes path 65 and is perpendicular to the plane of FIG. 3. The image of the curved surface is reconstructed from the X-ray attenuation data using substantially the same methods as are described herein with respect to reconstruction of planar oblique slices.

Similarly, the user could select a non-planar slice following a major blood vessel, such as the descending aorta, or a portion of the digestive tract. An image of the corresponding curved surface and/or a series of sectional slices through the vessel or digestive tract would be reconstructed, as described above.

Further alternatively, the user may indicate a sagittal or coronal cut for reconstruction, for example, a sagittal cut along body 22 in the plane of FIG. 3. In this case, scanner 20 will produce an image showing a sagittal cross-section through spinal cord 69, vertebrae 68, and disc spaces 67. In accordance with the present invention, this sagittal image is produced by back-projection directly from the attenuation values, as will be described below, rather than by interpolation between previously reconstructed axial image slices.

Preferably, after the user has indicated the course of path 65 and/or the positions, orientations, and any other desired quality factors regarding slices 66, such as slice thickness, scanner 20 automatically determines the scan extent and other scan parameters. These parameters preferably include selection of optimal axial planes for interpolation and back-projection, as described below, to produce oblique slices 66 or the image of the curved surface following path 65, with desired image quality and with minimal radiation dosage to subject 22 and/or minimal computing time.

Preferably, oblique slices 66 are reconstructed by circuitry 40, stored in memory 42, displayed by display unit 44, and otherwise printed and/or processed as appropriate, without necessarily reconstructing, storing, displaying, printing, etc., any axial image slices.

Alternatively, the user may designate one or a sequence of oblique slices using any suitable method of scan planning known in the art, for example, as described in the above mentioned U.S. Pat. 4,674,046. Furthermore, if the attenuation data or, more preferably, the preprocessed or filtered attenuation values from a spiral scan have been stored in memory, as described above, the user may also designate oblique slices for reconstruction, in accordance with the methods described herein, after the scan has been completed.

Returning now to FIG. 2, after the sequence of slices 50, 52, 54, etc., is selected, a plurality of parallel back-projection lines are defined within each slice, as illustrated in FIG. 2 by lines 60, 62 and 64 across slice 50. Each line 60, 62, 64 is defined by the intersection of the plane of oblique slice 50 with one of a plurality of axial planes 70, 72, 74, etc. through the body. Preferably, the same axial planes 70, 72, 74, etc., are used to define parallel back-projection lines on each of the sequence of slices 50, 52, 54, etc. Axial planes 70, 72, 74 are preferably equally spaced, although this spacing may be varied. As will be apparent from the description that follows, this spacing is a factor in determining the quality of the reconstructed image, including resolution, artifacts and noise in oblique slices 50, 52, 54. The spacing of planes 70, 72 and 74 is preferably chosen so that the image slices have desired quality. It will be appreciated that although, for clarity of illustration planes 70, 72 and 74 are show schematically in FIG. 2 as being relatively widely spaced, in practice the planes are preferably close together, spaced by a distance in the Z direction that is generally small compared to the extent of the slices in the x and y directions.

As X-ray tube 28 advances along its helical path, the attenuation signals are acquired in multiple views and are preprocessed and, preferably, filtered, as described above. The resultant attenuation data are interpolated to generate effective attenuation values with respect to each of axial planes 70, 72, 74, etc. Any suitable method of interpolation may be used to derive the effective attenuation values from the helical scan attenuation data, for example, methods described in U.S. patent application Ser. No. 08/556,824, filed Nov. 2, 1995, entitled "Multiple Slice CT Scanner," and in Israeli patent application no. 119,033, filed Aug. 7, 1996, entitled "Multi-Slice Detector Array," which are assigned to the assignee of the present application, and whose disclosures are incorporated herein by reference.

In some preferred embodiments of the present invention, the effective attenuation values are back-projected to determine CT values along back-projection line 60 in oblique slice 50, as well as in corresponding back-projection lines at the intersections of slices 52, 54, etc., with plane 70. CT values along lines 62 and 64, as well as in corresponding lines in slices 52, 54, etc., are similarly derived. For each oblique slice, the CT values for the corresponding plurality of axial lines are used to directly reconstruct and display a corresponding image of the entire oblique slice.

Preferably, oblique coordinate axes (X',Y') for back-projection operations are defined in axial planes 70, 72, 74. The oblique axes are rotated by an angle $\phi$ relative to the normal (X,Y) coordinate axes of scanner 20, so that one of the oblique axes, for example, the Y'-axis, is parallel to lines 60, 62 and 64. The rotation angle $\phi$ is generally equal to the projection of the slice orientation angle $\theta$ onto the X-Y plane. By rotation the axes in this way, all the points along each of lines 60, 62 and 64 will have the same X'-coordinate, and the operations will be further simplified. More preferably, the origin of the oblique axes is translated by a displacement $\delta$ in one or both of the X- and Y-directions, so that the Y'-axis, for example, is substantially congruent with one of lines 60, 62 and 64. Furthermore, the origin may be translated in this manner by a different displacement for each of lines 60, 62 and 64 in turn.

Back-projection to determine the CT values in slice 50 is performed only along each of the back-projection lines 60, 62 and 64, rather than in the entire axial planes 70, 72 and 74, thus saving considerable computation time by comparison with methods of oblique slice reconstruction known in the art. More than 90% of the computing time needed for the back-projection portion of reconstruction, which typically takes 20–30% of the total computing time, may be saved by calculating only one line 60 out of the total plane 70, instead of 512 lines, as is standard. Further computing time may be saved in filtering the attenuation data, if data corresponding to rays that are not used in back-projecting line 60 are eliminated from the filtering operation.

By back-projecting the effective attenuation values directly to line 60, and similarly for the other axial back-projection lines, oblique slices 50, 52, 54, etc., may be reconstructed with image resolution approaching as closely as possible that which could be obtained in axial image slices reconstructed from the same scan of CT scanner 20. Although as described above, resolution in scanner 20 is generally non-isotropic, multiple closely-spaced, parallel oblique slices may be reconstructed in this manner and then "fused," i.e., added together, in order to provide a sum slice having substantially angle-independent resolution and thus improve the image quality of the slices obtained by the fusion. The thickness of each slice, i.e., the resolution in the direction of slice axis 56, is substantially constant over the entirety of each slice.

Alternatively, a substantially similar result may be obtained by "fusing" together preprocessed attenuation values or preprocessed and filtered values from multiple closely spaced axial planes. These values are added or averaged together, preferably by weighted averaging, to produce attenuation sum values for each of planes 70, 72, 74, etc. The sum values arc then back-projected to find CT values along lines 60, 62, 64, etc., as described above. By "fusing" the attenuation values, rather than reconstructing and then fusing multiple oblique slices, computation time in reconstructing the oblique sum slice may be reduced.

By contrast with the methods described hereinabove, when oblique slices are reconstructed by interpolation of axial slice CT image values after back-projection of the axial slices, in accordance with methods known in the art, the image quality in the oblique slices is typically degraded, because there are two interpolation steps: first to determine the effective attenuation values in the axial slices, and second to find the CT image values in the oblique slice. The thickness of the interpolated oblique slices is not clearly defined, since CT image values at different points in the oblique slice are interpolated from different axial slices using different weighting factors in the interpolation. Thus, the present invention provides not only faster reconstruction of oblique CT image slices, but also images of better quality.

Figure 4:
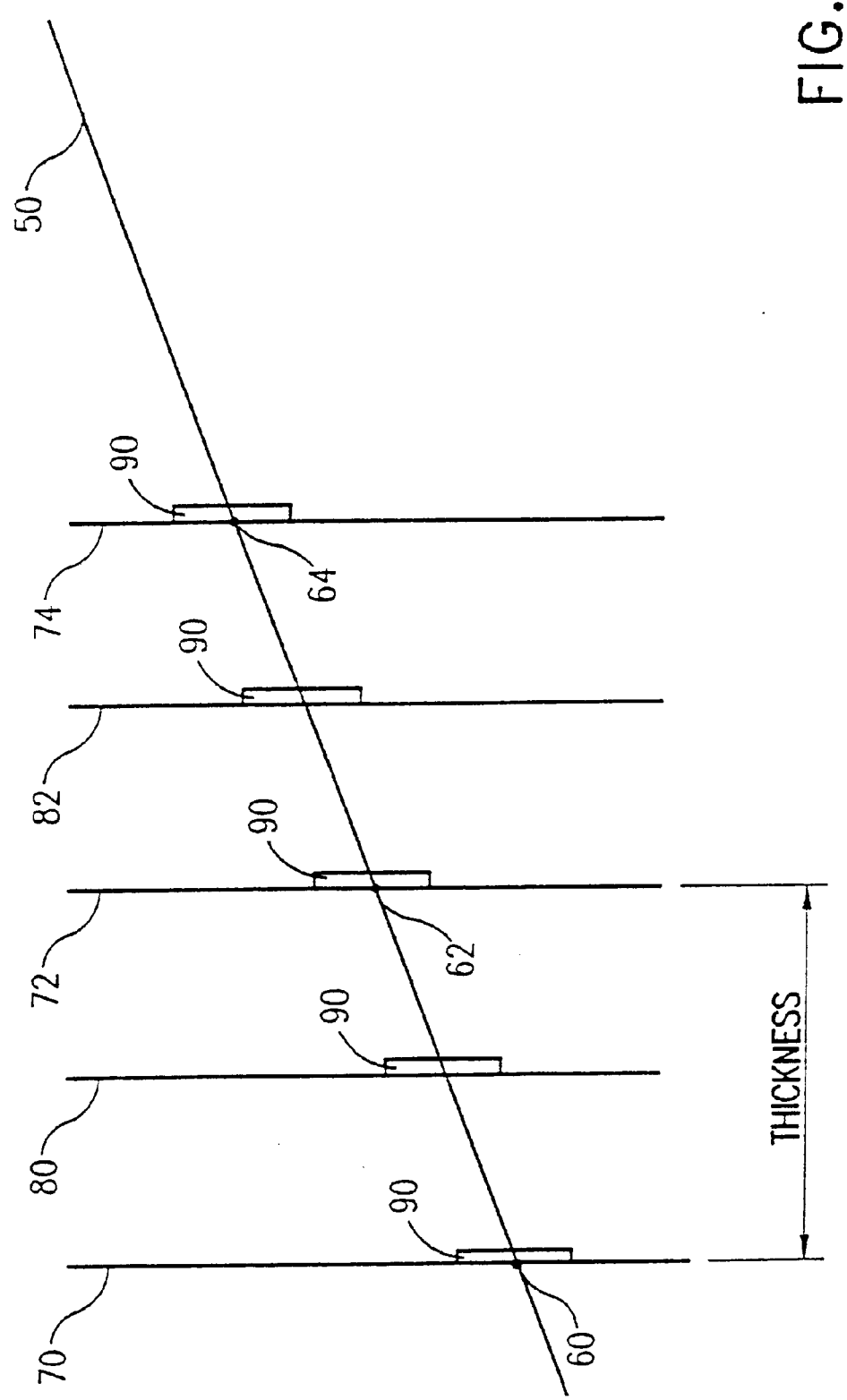
FIG. 4 is a schematic illustration showing a side view of an oblique image slice and axial planes in the scanner of FIG. 1, exemplifying aspects of another method for CT image reconstruction in accordance with a preferred embodiment of the present invention.

FIG. 4 schematically illustrates another preferred embodiment of the present invention, in which oblique image slice 50 (and, similarly, slices 52, 54, etc.) is reconstructed by back-projection of effective attenuation values in axial planes 70, 72 and 74, as well as from additional, intervening axial planes 80 and 82. Slice 50 and planes 70, 72, 74, 80 and 82 are shown in FIG. 4 in side view. Slices 52 and 54 are omitted from FIG. 4 for clarity of illustration, but it will be understood that the images corresponding to these slices are derived similarly to that of slice 50. CT image values along line 60 are found by back-projecting the effective attenuation values in plane 70, as described above, and likewise along the lines of intersection of plane 50 with planes 72, 74, 80 and 82.

As noted above, planes 70, 72 and 74 are preferably mutually spaced by an axial distance generally equal to the thickness of axial image slices to be reconstructed at these planes. Plane 80, in between planes 70 and 72, is preferably spaced from each of planes 70 and 72 by a distance generally equal to half the thickness, and similarly for plane 82 between planes 72 and 74. Thus, the plurality of axial planes 70, 80, 72, 82, 74, and so forth, are mutually spaced along the spiral path described by the X-ray tube by a distance that is generally equal to or less than half the thickness of the corresponding axial image slices.

It has been found that by spacing axial planes 70, 80, 72, 82, 74, etc., by a distance equal to or less than half the thickness of such axial slices, image artifacts that are encountered in prior art methods of oblique slice interpolation are substantially eliminated. Image quality is further improved, although at the expense of increased computing time, if the axial planes are spaced still more closely, for example, by a distance less than one third the axial slice thickness. It will be appreciated, furthermore, that this method of adding intervening axial planes, such as planes 80 and 82, can be used most effectively to eliminate artifacts in spiral-scan CT systems, in which the scan path of tube 28 allows attenuation data to be acquired at a no continuum of axial locations. The method will be less effective in axial-scan CT systems, in which the attenuation data arc acquired at a plurality of separate, mutually-spaced axial locations.

Additionally, CT image values may be found at other points in a vicinity 90 of line 60 within plane 70, and in similar vicinities within planes 72, 74, 80 and 82. These CT image values are preferably used to produce multiple, closely-spaced oblique image slices, parallel to slice 50, which may be fused in order to enhance the image quality of slice 50, as described above. Although slice 50 is a planar slice, it will be appreciated that the quality of images of non-planar surfaces may similarly be improved in this manner.

The CT image values found in vicinities 90 in axial planes 70, 72, 74, 80 and 82, may further be processed using image processing methods known in the art so as to improve the quality of the image of oblique slice 50 derived therefrom. For example, the CT values in vicinities 90 may be used to detect ring artifacts, so that the artifacts may be more easily identified and eliminated from slice 50. Ring artifacts commonly appear in axial CT images, as circles, centered at the center of revolution of tube 28. The artifacts are preferably automatically recognized by an image processing computer associated with CT scanner 20, which analyzes the CT image values in vicinities 90 of the axial planes, using image processing methods known in the art. The artifacts are then removed from oblique slice images 50, 52, 54 during post-processing, as is known in the art. for example, by interpolating between CT values of points adjacent to the locations of the artifacts. This method of artifact correction may similarly be used in post-processing of images of non-planar surfaces.

Alternatively, ring artifacts may be identified and processed directly in oblique slices 50, 52, 54. The ring artifacts will appear in the oblique slice images as ellipses or portions of ellipses, centered at the center of revolution of tube 28. (In particular, when the oblique slice angle θ is near 90 degrees, only a portion of the ellipse may be contained within the slice.) These ellipses will have a known ratio of major to minor axes, and a known orientation of these axes in the oblique slice planes, dependent on the slice angle θ. Preferably, the image processing computer described above is programmed to recognize and remove from oblique slice images 50, 52, 54 ellipses and portions of ellipses centered at the center of revolution and having the known major-to-minor-axis ratio and/or axis orientation.

Although the above preferred embodiments have generally been described in terms of single oblique image slices or multiple oblique parallel slices of equal thicknesses, it will be understood that the principles of the present invention may similarly be applied to reconstruct from a single scan multiple, non-parallel slices, as illustrated in FIG. 3, as well as multiple slices of different thicknesses. Slices of greater and lesser thicknesses may be reconstructed from the same scan, for example, by fusing together attenuation values from multiple axial planes or by reconstructing and fusing together a number of slices to make up the slices of greater thickness, as described above, or by varying the spacing of axial planes 70, 72, 74 etc. Slices of different thicknesses are useful in examining the head and brain of a subject, for example.

Furthermore, when preprocessed or filtered attenuation data have been stored in memory, as described above, additional oblique slices, at various slice angles and positions. may be reconstructed in accordance with the principles of the present invention after the CT scan has been completed.

It will be appreciated that the preferred embodiments described above are cited by way of example, and the full scope of the invention is limited only by the claims.

What is claimed is:

1. A method for reconstructing one or more non-axial image slices in a CT scanner, comprising:

reconstructing the one or more oblique or non-planar image slices, by processing X-ray attenuation data acquired over an axial range, to determine CT values at a plurality of points along one or more surfaces corresponding respectively to each of one or more oblique or non-planar image slices; and removing ring artifacts from the reconstructed images, wherein processing the attenuation data comprises back-projecting the data directly to the plurality of points along each of the one or more surfaces.

2. A method according to claim 1, the data is acquired over a range defined by an axial extent of the one or more oblique or non-planar image slices.

3. A method according to claim 1 wherein back-projecting the data comprises back-projecting the data to determine CT values substantially only at or in the vicinity of the plurality of points in each of the one or more oblique or non-planar slices.

4. A method according to claim 1, wherein the X-ray attenuation data is acquired along a spiral scan path traversing the range.

5. A method according to claim 1 wherein the reconstructed slices are curved non-planar slices constructed over one or more curved surfaces and wherein reconstructing the attenuation data to determine CT values along the one or more slices comprises processing the data to determine CT values at points along the curved surfaces.

6. A method according to claim 1, wherein the reconstructed slices are oblique image slices, oriented obliquely relative to an axis of the scanner, and wherein processing the attenuation data to determine CT values along the one or more slices comprises processing the data to determine CT values at points in one or more oblique planes defined by the image oblique slices.

7. A method according to claim 6 wherein the ring artifacts are detected and corrected on the reconstructed oblique image.

8. A method according to claim 7 wherein said ring artifacts are detected in the one or more oblique image slices by identifying at least a portion of an ellipse in at least one of the oblique image slices.

9. A method according to claim 8, wherein identifying at least a portion of the ellipse comprises finding an ellipse having a known ratio of major to minor axes.

10. A method according to claim 8, wherein identifying at least a portion of the ellipse comprises finding an ellipse having a known angular orientation of its axes in the plane of one of the one or more oblique image slices.

11. A method according to claim 5 or claim 6 wherein removing ring artifacts comprises:
  selecting a plurality of axial planes, which define a plurality of lines at the respective intersections of the axial planes with the one or more oblique or non-planar slices, along which lines the CT values are determined; and
  processing the X-ray attenuation data to determine CT values at additional points in a vicinity of one or more of the lines in at least one of the axial planes.

12. A method according to claim 11 wherein removing ring artifacts includes detecting artifacts in the at least one of the axial planes using the CT values at the additional points.

13. A method according to claim 1, wherein processing the attenuation data to determine CT values comprises pre-processing the attenuation data during a CT scan, storing the pre-processed data, and processing the stored data to determine the CT values.

14. A method for reconstructing one or more oblique or non-planar image slices in a CT scanner, comprising:
  selecting a plurality of axial planes, having a predetermined axial spacing therebetween, thereby defining a plurality of lines at the intersections of the planes with the one or more non-axial image slices;
  acquiring X-ray attenuation data along a spiral scan path having a known pitch traversing an axial range defined by the plurality of axial planes; and
  processing the X-ray attenuation data to determine CT values directly only at a plurality of points along the plurality of lines and in the axial planes only in a vicinity of the lines.

15. A method according to claim 14 wherein processing the attenuation data comprises filtering the attenuation data before back-projecting the data, and wherein data that are not used to determine the CT values along the plurality of lines or their vicinity are eliminated from the filtering operation.

16. A method according to claim 14, wherein processing the attenuation data comprises interpolating the attenuation data to find effective attenuation values in the plurality of axial planes.

17. A method according to claim 14, wherein selecting the plurality of axial planes comprises selecting axial planes mutually spaced by a distance substantially less than the thickness of an axial image slice corresponding to one of the axial planes.

18. A method according to claim 17, wherein selecting axial planes mutually spaced by a distance substantially less than or equal to the thickness of the axial image slice corresponding to one of the axial planes comprises selecting axial planes mutually spaced by a distance less than or equal to half the thickness of the axial image slice.

19. A method according to claim 18, wherein selecting axial planes mutually spaced by a distance substantially equal to or less than half the thickness of the axial image slice corresponding to one of the axial planes comprises selecting axial planes mutually spaced by a distance less than or equal to one third the thickness of the axial image slice.

20. A method for reconstructing a plurality of non-axial image slices in a CT scanner, comprising:
  selecting a position and an orientation for each of the plurality of oblique or non-planar slices; and
  reconstructing each of the slices according to the method of claim 14, wherein selecting the plurality of axial planes comprises selecting at least one common axial plane for reconstructing at least a portion of each of two of the plurality of oblique or non-planar slices.

21. A method according to claim 20, wherein slices are oblique slices, and wherein selecting the position and the orientation for each of the plurality of oblique slices comprises selecting a common orientation for at least two of the oblique slices.

22. A method according to claim 21, wherein selecting the position and orientation for each of the plurality of oblique slices comprises selecting a common orientation for a group of at least three of the oblique slices and selecting the positions of the slices so that the slices in the group are evenly spaced.

23. A method according to claim 21, and comprising fusing at least two of the commonly-oriented oblique slices to produce an oblique sum slice.

24. A method according to claim 23, wherein fusing the at least two commonly-oriented oblique slices to produce an oblique sum slice comprises producing a sum slice having angle-independent resolution.

25. A method according to claim 24, wherein selecting the position and orientation for each of the plurality of oblique slices comprises selecting a common orientation for a group of at least three of the oblique slices and selecting the positions of the slices so that the slices in the group are unequally spaced.

26. A method according to claim 20, wherein selecting the position and orientation for each of the plurality of slices comprises selecting different orientations for at least two of the slices.

27. A method according to claim 14 wherein processing the X-ray attenuation data comprises fusing attenuation data from multiple, mutually-adjacent planes among the plurality of axial planes to produce sum data, and wherein back-projecting the attenuation data comprises back-projecting the sum data.

28. A method according to claim 14, wherein processing the attenuation data to determine CT values comprises pre-processing the attenuation data during a CT scan, storing the pre-processed data, and processing the stored data to determine the CT values.

29. A method according to claim 28, wherein pre-processing the data comprises filtering the data.

\* \* \* \* \*